United States Patent [19]

Janchitraponvej et al.

[11] Patent Number: 5,556,616

[45] Date of Patent: Sep. 17, 1996

[54] STABLE CONDITIONING SHAMPOO HAVING A HIGH FOAM LEVEL CONTAINING A GRAFT COPOLYMERS OF POLYETHYLENEIMINE AND SILICONE AS A CONDITIONER

[75] Inventors: Ben Janchitraponvej, Niles; William Brown, Flossmoor, both of Ill.

[73] Assignee: Helene Curtis, Inc., Chicago, Ill.

[21] Appl. No.: 298,944

[22] Filed: Aug. 31, 1994

Related U.S. Application Data

[63] Continuation-in-part of Ser. No. 62,606, May 17, 1993, Pat. No. 5,417,965, which is a continuation-in-part of Ser. No. 719,818, Jun. 24, 1991, Pat. No. 5,221,530.

[51] Int. Cl.$^6$ .................................................. A61K 7/075
[52] U.S. Cl. .................. 424/70.122; 424/70.11; 424/70.12
[58] Field of Search ............... 424/70.122, 70.12, 424/70.11, 70.1

[56] References Cited

U.S. PATENT DOCUMENTS

| | | | |
|---|---|---|---|
| 3,761,417 | 9/1973 | Parran | 252/106 |
| 4,252,656 | 2/1981 | Liebowitz et al. | 252/8.8 |
| 4,311,626 | 1/1982 | Ona et al. | 524/500 |
| 4,344,763 | 8/1982 | Tolgyesi et al. | 8/127.51 |
| 4,381,259 | 4/1983 | Homma et al. | 252/542 |
| 4,559,227 | 12/1985 | Chandra et al. | 424/70.122 |
| 4,586,518 | 5/1986 | Cornwall et al. | 132/206 |
| 4,663,158 | 5/1987 | Wolfram et al. | 424/70.11 |
| 4,728,457 | 3/1988 | Fieler et al. | 252/174.15 |
| 4,741,855 | 5/1988 | Grote et al. | 252/142 |
| 4,749,732 | 6/1988 | Kohl et al. | 524/43 |
| 4,940,576 | 7/1990 | Walsh | 424/70.16 |
| 5,034,218 | 7/1991 | Duvel | 424/70.12 |
| 5,104,645 | 4/1992 | Cardin et al. | 514/345 |
| 5,118,498 | 6/1992 | Helioff et al. | 424/70.11 |
| 5,183,601 | 2/1993 | Jisai et al. | 252/524 |

FOREIGN PATENT DOCUMENTS

479000A2  4/1992  European Pat. Off. .

OTHER PUBLICATIONS

CTFA Cosmetic Ingredient Handbook (First Edition) published by The Ccosmetic, Toiletry and Fragrance Association, Inc., Copyright© 1988, pp. 56–58, 71–73 and 319.
Petrach Systems product/pricing publication.

*Primary Examiner*—Melvyn I. Marquis
*Assistant Examiner*—Robert H. Harrison
*Attorney, Agent, or Firm*—Marshall, O'Toole, Gerstein, Murray & Borun

[57] ABSTRACT

A conditioning shampoo containing an anionic cleansing surfactant, in an amount of about 5% to about 65% by weight, preferably about 5% to about 25% by weight, e.g., ($C_{12}$–$C_{22}$) alkyl sulfate, and/or a long chain ($C_{12}$–$C_{22}$) partially or fully ethoxylated alkyl sulfate, and/or a long chain ($C_{12}$–$C_{22}$) alkyl sulfonate, and a copolymer of polyethyleneimine and a silicone in an amount of about 0.1% to about 20% by weight, preferably about 0.1% to about 10% by weight. The composition, provides excellent foaming, conditioning and stability, without settling of water-insoluble materials.

20 Claims, No Drawings

STABLE CONDITIONING SHAMPOO HAVING A HIGH FOAM LEVEL CONTAINING A GRAFT COPOLYMERS OF POLYETHYLENEIMINE AND SILICONE AS A CONDITIONER

CROSS REFERENCE TO RELATED APPLICATION

This application is a continuation-in-part of application U.S. Ser. No. 08/062,606 filed May 17, 1993, now U.S. Pat. No. 5,417,965, which is a continuation-in-part of U.S. Ser. No. 07/719,818 filed Jun. 24, 1991, now U.S. Pat. No. 5,221,530 issued Jun. 22, 1993.

FIELD OF THE INVENTION

The present invention is directed to a hair conditioning shampoo composition and to a method of treating hair with the composition to provide the hair with improved wet stage and dry stage conditioning properties as well as other conditioning properties, such as softness, without residual build-up of conditioning agents on the hair. The conditioning shampoo also thoroughly cleanses the hair, while conditioning, with a cleansing detergent that develops an unexpectedly high foam level and unexpected stability. The conditioning shampoo contains an anionic detergent, and a conditioner that is a graft copolymer of polyethyleneimine (PEI) on a silicone polymer backbone, e.g. polymethylsiloxane. More particularly, the present invention is directed to a hair conditioning shampoo composition including one or more anionic cleansing surfactants, such as ammonium lauryl sulfate (ALS) or ammonium lauryl ether sulfate (ALES), and a PEI-silicone copolymer conditioner, that is stable over extended periods of time at elevated temperature.

Surprisingly, the composition develops copious amounts of foam for a conditioning shampoo while achieving excellent conditioning benefits, and is unexpectedly stable without requiring suspending agents normally required to suspend silicone conditioning agents, and provides excellent foaming and cleansing with a smaller amount of strong anionic cleansing detergents, such as a long chain alkyl sulfate, or a partially ethoxylated long chain alkyl sulfate or sulfonate, e.g., about 10% to about 15% active vs. about 18% to about 21% active anionic surfactants used in prior art silicone conditioning agent containing shampoos.

BACKGROUND OF THE INVENTION AND PRIOR ART

Soiled human hair is shampooed to remove sebum that is naturally secreted by the head as well as soil and other atmospheric contaminants that accumulate on the hair. Sebum, in particular, accumulates on the hair in a relatively short period of time leaving the hair with a greasy, dirty feel and poor manageability. The most effective shampoos for cleansing the hair, for removal of the atmospheric contaminants and sebum, are those that contain high lather synthetic anionic detergents, such as the long chain alkyl sulfates, the partially ethoxylated long chain alkyl sulfates and the long chain sulfonates. These synthetic anionic detergents are very effective for cleansing the hair but, after rinsing with water, leave the hair with a dried touch, usually called "creak" and result in hair, when wet, that is in an extremely tangled and unmanageable after-shampoo condition.

Thoroughly cleansed hair is extremely difficult to comb, in either the wet or dry state because the individual hair fibers tend to snarl, kink, and interlock with each other. Particularly prior to complete drying of thoroughly cleansed hair, in this after-shampoo stage, the hair is very difficult to comb or brush. Even after complete drying, the thoroughly cleansed hair remains difficult to comb or brush and does not set well. Thoroughly clean, dried hair also has undesirable electrostatic properties in a low humidity atmosphere that causes the hair to "fly away," thereby further reducing the combing or brushing property of the hair. Generally, these above-outlined problems that result from synthetic detergent cleansing of the hair, particularly for the high-lather synthetic anionic detergents, have been alleviated either by the after-shampoo treatment of the hair with hair conditioners, for example, in the form of a hair rinse, or by including hair conditioners directly within the shampoo composition.

After-shampoo hair conditioning compositions are easily formulated but are inconvenient to use because of the necessity of applying the conditioner to the hair in a separate stage, after shampooing. The preparation of a conditioning shampoo has been more difficult because of inherent incompatibility problems between anionic surfactants and the cationic compounds that are good conditioning agents. Contact between an anionic surfactant and a cationic surfactant or cationic polymer produces a precipitate that forms immediately or causes an interaction between the anionic and cationic compounds that significantly reduces their respective cleaning and conditioning properties, and especially a very noticeable severe loss of foam attributed by the anionic cleansing surfactant. The reduction in cleansing and conditioning effectiveness is observed even in compositions wherein the anionic and cationic compounds do not precipitate from the composition but remain in solution or suspension. This incompatibility between an anionic surfactant and a cationic conditioning compound is well recognized by those skilled in the art. For example, Sagarin in *Cosmetics*, Interscience Publishers, Inc., New York, p. 538 (1957), states that anionic and cationic compounds cannot be used in combination because they react to form insoluble salts.

A partial solution to this incompatibility problem in the formulation of conditioning shampoos is exemplified by the following patents that disclose compositions that contain surfactants that are not anionic, e.g., nonionics, amphoterics and zwitterionics together with cationic conditioning compounds: U.S. Pat. No. 3,849,348 to Hewitt; U.S. Pat. No. 3,990,991 to Gerstein; and U.S. Pat. No. 3,822,312 to Sato.

Another problem inherent in formulating a conditioning shampoo is an instability problem that results when water-insoluble conditioning agents are also included in the conditioning shampoo composition, such as the nonvolatile silicones that are well recognized in the art as providing a degree of softness to the hair.

Silicones in shampoo compositions have been disclosed in a number of different patents: U.S. Pat. No. 2,826,551, Mar. 11, 1958 to Green; U.S. Pat. No. 3,964,500, Jun. 22, 1976 to Drakoff; U.S. Pat. No. 4,364,837, Dec. 21, 1982 to Pader; British Patent No. 849,433, Sept. 28, 1960 to Woolston; U.S. Pat. No. 4,741,855 to Grote etal.; U.S. Pat. Nos. 4,788,006 and 4,902,499 to Bolich, Jr. et al.; U.S. Pat. No. 4,704,272 to Oh et al.; and Janchitraponvej U.S. Pat. Nos. 4,954,335 and 5,328,685. The silicones are well known to substantially reduce the foaming of anionic cleansing surfactants.

A particularly difficult problem to solve in silicone-containing conditioning shampoos is that of providing a conditioning shampoo that provides excellent cleansing of the hair while providing high foaming and, at the same time, also has excellent conditioning performance.

Polyethyleneimine is disclosed as a separate component for a conditioning shampoo in our parent application, and provides excellent wet combing benefits but does not significantly improve dry combing. While the addition of a silicone fluid and/or silicone gum to a conditioning shampoo improves dry feel, the silicones require the use of a suspending agent, and lower the amount of foam generated during shampooing.

The capability of providing excellent conditioning, cleansing and foam levels is achieved, with the compositions of the present invention, by incorporating into a shampoo formulation a conditioning agent that is a copolymer of polyethyleneimine on a silicone polymer backbone.

SUMMARY OF THE INVENTION

In brief, the present invention is directed to a method and composition for simultaneously shampooing and conditioning hair, while maintaining foam, that includes an aqueous carrier; an anionic cleansing surfactant, such as an alkyl sulfate or an alkyl ether sulfate, in an amount of about 5% to about 65% by weight; and a polyethyleneimine-silicone copolymer conditioning agent, in an amount of about 0.01% to about 20% by weight.

The composition has extended product stability, excellent overall conditioning to human hair, particularly superior wet and dry combing properties, and unexpectedly maintains very high levels of foam.

It was further surprisingly and unexpectedly found that hair treated with the compositions of the present invention is thoroughly cleansed at high foam levels and exhibits improved physical and cosmetic properties, such as gloss, wet combing, dry combing, thickness, manageability, softness and body.

Therefore, an aspect of the present invention is to provide a hair-treating composition that cleanses the hair and imparts improved physical properties and cosmetic properties to the hair in a single application from a mild conditioning shampoo that develops unexpectedly high foam quantities.

Another aspect of the present invention is to provide a physically stable conditioning shampoo containing an anionic surfactant, and a copolymer of polyethyleneimine and a silicone polymer that provide hair conditioning and composition stability, wherein the composition develops excellent foam levels and can be formulated at room temperature.

Another aspect of the present invention is to provide a new and improved conditioning shampoo containing a strong anionic detergent, such as a long chain alkyl sulfate, long chain alkyl ether sulfate, and/or long chain sulfonate, that is compatible with cationic conditioning agents, and that maintains an unexpectedly high foam level although the composition contains a PEI-silicone copolymer conditioning agent.

Still another aspect of the present invention is to provide a new and improved conditioning shampoo including about 5% to about 25% of an anionic surfactant; and about 0.01% to about 20% preferably about 0.5% to about 10%, of a polyethyleneimine-silicone copolymer that surprisingly provides composition stability and added conditioning benefits, particularly increased wet and dry combing and reduced static (fly away) for better manageability; and optionally any known emulsion stabilizer and/or a viscosity increasing agent for added stability of aqueous emulsions, each in an amount of about 0% to about 10% by weight, active, preferably about 0.1% to about 5% by weight.

A further aspect of the present invention is to provide a new and improved method of cleansing and conditioning hair, simultaneously, with a composition containing one or more anionic surfactants; and a polyethyleneimine-silicone copolymer conditioning agent, while providing high foam levels, and excellent cleansing, excellent conditioning in a stable conditioning shampoo.

Still another aspect of the present invention is to provide a new and improved conditioning shampoo having a pH in the range of about 4 to about 10, preferably about 5 to about 7, including about 5% to about 65% of an anionic surfactant; and a polyethyleneimine-silicone copolymer in an amount of about 0.01% to about 20%, preferably about 0.05% to about 10% by weight.

Another object of the present invention is to provide a new and improved conditioning shampoo having a pH in the range of about 4 to about 10, preferably about 5 to about 7, including about 5% to about 65% of an anionic surfactant; and a copolymer of a polyethyleneimine grafted onto a silicone polymer backbone, in an amount of about 0.01% to about 20%, preferably about 0.05% to about 10% by weight.

The above and other aspects and advantages of the present invention will become apparent from the following detailed description of the preferred embodiments.

DETAILED DESCRIPTION OF THE PREFERRED EMBODIMENTS

The aqueous conditioning shampoo compositions of the present invention generally include water in an amount of about 60% to about 80–90% by weight; and an anionic surfactant preferably in an amount of about 5% to about 25% by weight of the composition; a copolymer of poleythyleneimine and a silicone polymer, preferably a siloxane, in an amount of about 0.01% to about 20%, preferably about 0.05% to about 10% by weight.

The conditioning shampoo of the present invention provides the hair with improved physical and cosmetic conditioning properties, such as gloss, thickness, softness, and manageability, including excellent wet and dry combing properties and body simultaneously with excellent cleansing at high foam levels in a mild conditioning shampoo. As will be demonstrated more fully hereinafter, it is surprising and unexpected that the composition of the present invention, including an anionic cleansing detergent, and a cationic PEI-silicone copolymer conditioning compound is able to provide the demonstrated cleansing at such a high foam level in a stable composition containing a silicone conditioning agent.

The anionic cleansing surfactant used in the composition and method of the present invention can be any of the anionic surfactants known or previously used in the art of hair shampoos. An anionic cleansing surfactant should be included in the composition of the present invention to effectively cleanse the hair and generates a high, stable foam level that consumers equate with cleaning efficiency. While nonionic and amphoteric surfactants have not been as effective in cleansing the hair and do not provide the high foam level desired by consumers, surprisingly, it has been found that the composition of the present invention provides excellent foam levels with the less strong anionic cleansing detergents or with the strong anionic detergents at levels generally below about 15% by weight of the composition, particularly when the foam level is boosted with one or more common foam boosters, such as a betaine or other foam booster. Optionally, nonionic amphoteric and/or zwitterionic surfactants can be included in the compositions of the present invention in addition to one or more anionic surfactants, to help stabilize foam, to provide a suitable viscosity, or to give other functional or esthetic properties to the composition.

Usually, the anionic cleansing surfactant includes a hydrophobic moiety, such as a carbon chain including from about eight carbon atoms to about 30 carbon atoms, and particularly from about 12 carbon atoms to about 22 carbon atoms and further includes a hydrophilic moiety, such as a sulfate, sulfonate, carbonate, phosphate or carboxylate. Often, the hydrophobic carbon chain is etherified, such as with ethylene oxide or propylene oxide, to impart a particular physical property, such as increased water-solubility or reduced surface tension, to the anionic cleansing surfactant.

Suitable anionic cleansing surfactants include, but are not limited to, compounds in the classes known as alkyl sulfates, alkyl ether sulfates, alkyl sulfonates, alkyl ether sulfonates, sulfate esters of an alkylphenoxy polyoxyethylene ethanol, alpha-olefin sulfonates, beta alkyloxy alkene sulfonates, alkyl arylsulfonates, alkyl carbonates, alkyl ether carboxylates, fatty acids, succinamates, sulfosuccinates, sarcosinates, octoxynol or nonoxynol phosphates, taurates, fatty taurides, sulfated monoglycerides, fatty acid amino polyoxyethylene sulfates and isothienates; or combinations thereof. Many additional anionic cleansing surfactants are described in McCUTCHEON'S DETERGENTS AND EMULSIFIERS, 1989 ANNUAL published by McCutcheon's Division MC Publishing Company, herein incorporated by reference. Usually, the anionic cleansing surfactant is present in the composition as a neutralized salt in the form of a sodium, potassium, lithium, ammonium. alkylammonium or hydroxyalkylammonium salt, wherein the alkyl moiety includes from one to about three carbon atoms.

Exemplary anionic cleansing surfactants that are useful in the composition and method of the present invention include, but are not limited to, the ammonium, monoethanolamine, diethanolamine, triethanolamine, isopropylamine, sodium, potassium, lithium, or magnesium salts of lauryl sulfate, dodecylbenzenesulfonate, lauryl sulfosuccinate, lauryl ether sulfate, lauryl ether carboxylate, lauryl sarcosinate, cocomethyl tauride, and sulfosuccinate half ester amide; or combinations thereof. Also useful are the zwitterionic betaines, e.g., cocamdopropyl betaine, cocamidopropyl hydroxysultaine, and the like; and the anionic carboxylate cleansing detergents, such as $C_{11}$–$C_{15}$ Pareth-7 carboxylic acid, $C_{11}$–$C_{15}$ Pareth-9, $C_{11}$–$C_{15}$ Pareth-12, $C_{11}$–$C_{15}$ Pareth-20, $C_{11}$–$C_{15}$ Pareth-30, $C_{11}$–$C_{15}$ Pareth-40, $C_{11}$–$C_{21}$ Pareth-10, $C_{12}$–$C_{13}$ Pareth-5 carboxylic acid, $C_{12}$–$C_{15}$ Pareth-2 phosphate, $C_{12}$–$C_{15}$ Pareth-7 carboxylic acid, $C_{12}$–$C_{15}$ Pareth-9, $C_{12}$–$C_{15}$ Pareth-12, $C_{14}$–$C_{15}$ Pareth-13, $C_{22}$–$C_{24}$ Pareth-33, cocaminobutyric acid, cocaminopropionic acid, coceth-7 carboxylic acid, cocoamphodipropionic acid, coconut acid, deceth-7 carboxylic acid, hydrogenated coconut acid, hydrogenated menhaden acid, hydrogenated tallow acid, hydroxystearic acid, isostearic acid, lanolin acid, lauraminopropionic acid, laureth-5 carboxylic acid, laureth-10 carboxylic acid, lauroamphodipropionic acid, linoleic acid, linolenic acid, linseed acid, MEA-laureth-6-carboxylate, myristaminopropionic acid, palmitic acid, sodium $C_{12}$–$C_{15}$ Pareth-6 carboxylate, sodium $C_{12}$–$C_{15}$ Pareth-7 carboxylate, sodium ceteth-13 carboxylate, sodium isosteareth-6 carboxylate, sodium isosteareth-11 carboxylate, sodium laureth-13 carboxylate, sodium trideceth-7 carboxylate, sodium trideceth-12 carboxylate, trideceth-4 carboxylic acid, trideceth-7 carboxylate, trideceth-15 carboxylic acid, and trideceth-19 carboxylic acid.

The following low-irritation surfactants are particularly useful in formulating a "baby" shampoo having high performance in terms of foam level and cleansing while achieving exceptional mildness:

ANIONICS

Disodium Laureth Sulfosuccinate;
Disodium Lauroamido MEA Sulfosuccinate;
Disodium Ricinoleamido MEA Sulfosuccinate;
Ceteareth-25-Carboxylic Acid;
Trideceth-7-Carboxylic Acid;
Pareth-25-6-Carboxylic Acid;
Trideceth-4-Carboxylic Acid;
Trideceth-19-Carboxylic Acid;
Sodium Trideceth-12-Carboxylate;
Sodium Ceteth-13-Carboxylate;
Laureth-5-Carboxylic Acid (SANDOPAN® LA8);
Sodium Laureth-13-Carboxylate;
Sodium Oleth-13-Carboxylate;
Sodium Ceteareth-5-Carboxylate;
Sodium Ceteareth-9-Carboxylate;
Isosteareth-6-Carboxylic Acid; and
Isosteareth-11-Carboxylic Acid.

NONIONICS

PEG 30 Glyceryl Mono Cocoate;
PEG 78 Glyceryl Mono Cocoate;
PEG 82 Glyceryl Mono Tallowate;
PEG 200 Glyceryl Mono Tallowate; and
PEG 20 Glyceryl Mono Tallowate.

AMPHOTERICS

Cocampho-Carboxyglycinate (VARION® 2C);
Lauroampho-Carboxyglycinate (VARION® 2L);
Cocamidopropyl Betaine; and
Cocamidopropyl Hydroxysultaine (VARION® CAS).

The ability to provide a conditioning shampoo that has excellent conditioning benefits, as well as excellent foaming and stability, has been a long-felt need in the conditioning shampoo art. The conditioning shampoos of the present invention solve this long-felt need by including a polyethyleneimine-silicone copolymer conditioning agent.

The polyethyleneimine(s) contained in the PEI-silicone copolymer conditioner portion of the conditioning shampoo of the present invention generally have the formula $(CH_2CH_2NH)_n$ wherein n has an average value of about 5 to about 2500. Specific examples of polyethyleneimines are PEI-7; PEI-15; PEI-30; PEI-45; PEI-1000; PEI-1500; and PEI-2500, wherein the integer following the PEI corresponds to the value of n in the formula above. The amount of PEI in the PEI-silicone copolymers can vary from about 20% to about 95% by weight of the PEI-silicone copolymer, and preferably is about 30% to about 90% by weight of the copolymer.

The PEI grafted onto the silicone backbone polymer also can be a polyethyleneimine having the following structural formula:

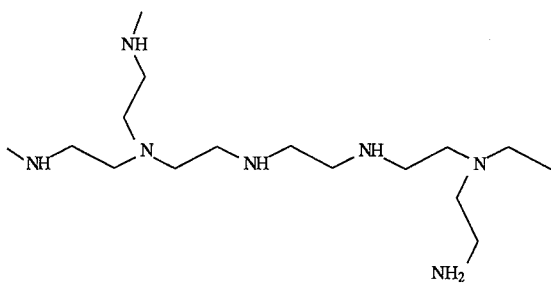

The molecular weight of the polyethyleneimine grafted onto the silicone backbone polymer is not critical and can be any molecular weight commercially available, e.g., polyethyleneimines available from BASF Corporation having a weight average molecular weight in the range of about 700 to about 70,000. The preferred polyethyleneimines have a ratio of primary:secondary:tertiary nitrogen atoms of about 1:2:1, respectively, and have a molecular weight in the range of about 700 to about 70,000.

One PEI-silicone copolymer useful in accordance with the present invention is available from Petrarch Systems, Bristol, Pa. under the trademark GLASSCLAD® IM, 50% solids in isopropanol, advertised as a glass coating useful to provide glass surfaces with greater affinity for tissue cells.

Another useful PEI-silicone copolymer is MACKAMER™ BW-147 by the McINTYRE Group Ltd., Chicago, Ill. MACKAMER BW-147 has the structure

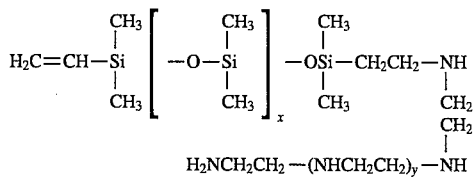

wherein X is about 700, and Y is about 900. Compounds similar to MACKAMER™ BW-147 also are useful in the conditioning shampoo of the present invention. Such compounds have the same structure as MACKAMER™ BW-147 except X is about 600 to about 800 and Y is about 900 to about 1,200. In addition, the terminal vinyl group of MACKAMER™ BW-147 can be replaced with a methyl group, a phenyl group, methoxy group or phenoxy group.

Other PEI-silicone copolymers also are envisioned for use in the present conditioning shampoo. For example, the reaction product of an amine-functionalized silicone and ethyleneimine provides a useful PEI-silicone. A silicone copolymer of desired molecular weight can be selected and reacted with a sufficient amount of ethyleneimine to provide a PEI-silicone copolymer having the desired amount of grafted PEI. One such amine-functionalized silicone is trimethylsilylamodimethicone.

In addition to an amine functionalized silicone, a silanol can be reacted with ethyleneimine to provide the PEI-silicone copolymer. Silanols have a reactive hydroxyl group that reacts with ethyleneimine and grafts the ethyleneimine onto the silicone backbone in the form of PEI. Exemplary silanols are dimethiconol, which has a terminal hydroxyl group, and dimethicone copolyol, which has ethylene oxide side chains.

Another useful PEI-silicone copolymer would be the nitrogen analogue of dimethicone copolyol. This PEI-silicone copolymer would be similar to dimethicone copolyol except the polyethylene glycol and polypropylene glycol side chains are replaced by PEI.

Another exemplary compound that can be reacted with ethyleneimine to provide a PEI-silicone copolymer include glycidoxypropyl methyldimethyl siloxane copolymer having the structure:

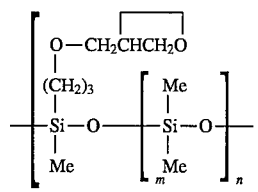

Other silicone compounds having a functionality that can react with ethyleneimine or a polyethyleneimine to provide a PEI-silicone copolymer useful in the present shampoo conditioner can be found in SILICON COMPOUNDS, Petrarch Systems, Bristol, Pa.

To achieve the full advantage of the present invention, an optional foam booster, in an amount of about 0.1% to about 20% by weight of the composition, is included in the composition to aid in the formation of copious amounts of foam. Suitable foam boosters include one or more of the following:

| | |
|---|---|
| Capramide DEA | Disodium Isostearyl Sulfosuccinate |
| Cetearyl Alcohol | Hydrogenated Tallow Amine Oxide |
| Cetyl Alcohol | Hydroxyethyl Hydroxypropyl $C_{12}$–$C_{15}$ Alkoxypropylamine Oxide |
| Cetyl Betaine | Hydroxyethyl Stearamide-MIPA |
| Cocamide | Isopropyl Stearate |
| Cocamide DEA | Isostearamidopropylamine Oxide |
| Cocamide MEA | Isostearamidopropyl Morpholine Oxide |
| Cocamide MIPA | Lauramide |
| Cocamidoethyl Betaine | Lauramide DEA |
| Cocamidopropylamine Oxide | Lauramide MEA |
| Cocamidopropyl Betaine | Lauramide MIPA |
| Cocamidopropyl Hydroxysultaine | Lauramidopropylamine Oxide |
| Cocamine Oxide | Lauramidopropyl Betaine |
| Cocoamphodipropionic Acid | Lauramine Oxide |
| Coco-Betaine | Lauryl Alcohol |
| Coco-Morpholine Oxide | Lauryl Betaine |
| Coconut Alcohol | Lauryl Sultaine |
| Coco/Oleamidopropyl Betaine | Myristamide DEA |
| Coco-Sultaine | Myristamide MEA |
| Cocoyl Hydroxyethyl Imidazoline | Myristamide MIPA |
| Cocoyl Sarcosinamide DEA | Myristamidopropylamine Oxide |
| DEA-Cocoamphodipropionate | Myristamidopropylamine Betaine |
| DEA-Lauraminopropionate | Myristamine Oxide |
| Decylamine Oxide | Myristaminoproionic Acid |
| Decyl Betaine | Myristyl Alcohol |
| Dihydroxyethyl $C_8$–$C_{10}$ Alkoxypropylamine Oxide | Myristyl Betaine |
| Dihydroxyethyl $C_9$–$C_{11}$ Alkoxypropylamine Oxide | Oleamidopropylamine Oxide |
| Dihydroxyethyl $C_{12}$–$C_{15}$ Alkoxypropylamine Oxide | Oleamidopropyl Betaine |
| Dihydroxyethyl Cocamine Oxide | Oleamidopropyl Hydroxysultaine |
| Dihydroxyethyl Stearamine | Oleamine Oxide |

| | |
|---|---|
| Oxide Dihydroxyethyl Tallowamine Oxide | Oleyl Betaine |
| | Palmamide DEA |
| Palmamide MEA | PEG-5 Lauramide |
| Palmamide MIPA | PEG-6 Lauramide |
| Palmamidopropyl Betaine | PEG-3 Lauramine Oxide |
| Palmitamide DEA | Sodium Cocoamphoacetate |
| Palmitamide MEA | Sodium Cocoamphopropionate |
| Palmitamidopropylamine Oxide | Sodium Lauraminopropionate |
| Palmitamidopropyl Betaine | Sodium Lauroamphopropionate |
| Palmitamine Oxide | Sodium Lauroyl Sarcosinate |
| Palm Kernel Alcohol | Sodium Myristoamphoacetate |
| Palm Kernelamide DEA | Sodium Myristoyl Sarcosinate |
| Palm Kernelamide MEA | Stearyl Alcohol |
| Palm Kernelamide MIPA | TEA-Hydrogenated Tallow Glutamate |
| Peanutamide MEA | TEA-Lauraminopropionate |
| Peanutamide MIPA | TEA-Myristaminopropionate |
| PEG-6 Cocamide | Tegobetaine L7 |
| | Undecylenamide DEA |
| PEG-3 Lauramide | Undecylenamide MEA |
| | Undecylenamidopropylamine Oxide |

One or more zwitterionic detergents, such as a betaine, in an amount of about 5% to about 25% by weight of the composition aids in stabilizing the composition but generally is not necessary to achieve a stable composition. Suitable betaines include, for example:

| | |
|---|---|
| Betaine | Myristamidopropyl Betaine |
| Cetyl Betaine | Myristyl Betaine |
| Cocamidoethyl Betaine | Oleamidopropyl Betaine |
| Cocamidopropyl Betaine | Oleamidopropyl Hydroxysultaine |
| Cocamidopropyl Hydroxysultaine | Oleyl Betaine |
| Coco-Betaine | Palmamidopropyl Betaine |
| Coco/Oleamidopropyl Betaine | Palmitamidopropyl Betaine |
| Coco-Sultaine | Ricinoleadmidopropyl Betaine |
| Decyl Betaine | Stearamidopropyl Betaine |
| Hydrogenated Tallow Betaine | Stearyl Betaine |
| Isostearamidopropyl Betaine | Tallowamidopropyl Betaine |
| Lauramidopropyl Betaine | Tallowamindopropyl Hydroxysultaine |
| Lauryl Betaine | Wheat Germamidopropyl Betaine |
| Lauryl Sultaine | |

Other compounds useful for composition stabilization, in an amount of about 0.1% to about 10% by weight of the composition include any one or more of the following:

| | |
|---|---|
| Acetylated Glycol Stearate | Maltodextrin |
| Aluminum Caprylate | Methoxy PEG-22/Dodecyl Glycol Copolymer |
| Aluminum Dilinoleate | Methylcellulose |
| Aluminum Distearate | Microcrystalline Cellulose |
| Aluminum Isostearates/Laurates/ Palmitates | Microcrystalline Wax |
| Aluminum | Montmorillonite |
| Isostearates/Laurates/ Stearates | |
| Aluminum | Myristyl Alcohol |
| Isostearates/Myristates | |
| Aluminum | Ozokerite |
| Isostearates/Palmitates | |
| Aluminum | Pectin |
| Isostearates/Stearates | |
| Aluminum Lanolate | PEG-2M |
| Aluminum Myristates/Palmitates | PEG-5M |
| Aluminum Stearate | PEG-7M |
| Aluminum Stearates | PEG-9M |
| Aluminum Tristearate | PEG-14M |
| Beeswax | PEG-20M |
| Bentonite | PEG-23M |
| $C_9$–$C_{11}$ Alcohols | PEG-45M |
| $C_{12}$–$C_{13}$ Alcohols | PEG-90M |
| $C_{12}$–$C_{15}$ Alcohols | PEG-115M |
| $C_{12}$–$C_{16}$ Alcohols | PEG-22/Dodecyl Glycol Copolymer |
| $C_{14}$–$C_{15}$ Alcohols | PEG-45/Dodecyl Glycol Copolymer |
| $C_{15}$–$C_{18}$ Glycol | Polyacrylic Acid |
| Calcium Carrageenan | Polyethylene |
| Calcium Stearate | Polyvinyl Acetate |
| Carbomer 910 | Potassium Alginate |
| Carbomer 934 | Potassium Carrageenan |
| Carbomer 934P | PVM/MA Copolymer |
| Carbomer 940 | PVP/VA Copolymer |
| Carbomer 941 | Saccharated Lime |
| Carboxymethyl Hydroxyethylcellulose | Sodium Acrylate/Vinyl Alcohol Copolymer |
| Carboxymethyl Hydroxypropyl Guar | Sodium $C_4$–$C_{12}$ Olefin/Maleic Acid Copolymer |
| Carrageenan | Sodium Carboxymethyl Dextran |
| Cellulose Gum | Sodium Carrageenan |
| Ceresin | Sodium Cellulose Sulfate |
| Cetearyl Alcohol | Sodium Polymethacrylate |
| Cetyl Alcohol | Sodium Polynaphthalene Sulfonate |
| Cholesterol | Sodium Polystyrene Sulfonate |
| Coconut Alcohol | Stearyl Alcohol |
| Ethylene/Acrylate Copolymer | Stearylvinyl Ether/Maleic Anhydride Copolymer |
| Ethylene/Vinyl Acetate Copolymer | Styrene/Maleic Anhydride Copolymer |
| Guar Gum | Synthetic Beeswax |
| Hydroxybutyl Methylcellulose | Synthetic Wax |
| Hydroxyethylcellulose | Tallow Alcohol |
| Hydroxyethyl Ethylcellulose | Tragacanth Gum |
| Hydroxypropylcellulose | |
| Hydroxypropyl Guar | Tridecyl Alcohol |
| Hydroxypropyl Methylcellulose | Xanthan Gum |
| Isopropyl Ester of PVM/MA Copolymer | |
| Karaya Gum | |
| Lanolin | |
| Lanolin Alcohol | |
| Lauryl Alcohol | |
| Locust Bean Gum | |

Other common cosmetic components and additives that can be incorporated into the conditioning shampoos of the present invention, as long as the basic properties of conditioning, cleansing and high foam levels are not adversely affected include, for example, fragrances, dyes, hair colorants, opacifiers, pearlescing agents, dandruff control agents, hydrotropes, foam stabilizers, solubilizers, preservatives, water softening agents, acids, bases, buffers and the lie. These optional components and additives usually will be present in weight percentages of less than about 2% each, and from about 5% to about 10% by weight in total.

The vehicle of the hair-treating composition is generally predominantly water, but organic solvents also can be used in order to help solubilize compounds that are not sufficiently soluble in water. Suitable solvents include the lower alcohols like ethyl alcohol and isopropyl alcohol; polyols like glycerol; glycols or glycol ethers, like 2-butoxyethanol, ethylene glycol, ethylene glycol monoethyl ether, propylene glycol and diethylene glycol monoethyl ether or monoethyl ether; and mixtures thereof. These non-aqueous solvents can be present in the hair-treating composition of the present invention in an amount from about 1% to 100% by weight and, in particular, from about 5% to about 50% by weight, relative to the total weight of the carrier vehicle in the composition.

The conditioning shampoos of the present invention also can be thickened, for example, with sodium alginate; guar gum; xanthan gum; gum arabic; cellulose derivatives such as methylcellulose, hydroxyethylcellulose, hydroxypropylmethylcellulose and carboxymethylcellulose; and various polymeric thickeners, such as polyacrylic acid derivatives. These thickeners are present in an amount ranging from about 0.1% to about 5%, and preferably from about 0.25% to about 1%, by weight relative to the total weight of the composition.

If instability of the composition is a problem, the composition also can include a suspending agent for the conditioning agent or other water-insoluble material, in an amount of about 0.5% to about 10%, by total weight of the composition. Suitable suspending agents are for example, distearyl amate (distearyl phthalamic acid); fatty acid alkanolamides; esters of polyols and sugars; polyethylene glycols; the ethoxylated or propoxylated alkylphenols; ethyoxylated or propoxylated fatty alcohols; and the condensation products of ethylene oxide with long chain amides. These suspending agents, as well as numerous others not cited herein, are well known in the art and are fully described in literature, such as McCUTCHEON'S DETERGENTS AND EMULSIFIERS, 1989 Annual, published by McCutcheon Division, MC Publishing Co.

The conditioning shampoos also can include other emulsifiers, inorganic salts, humectants and similar materials to provide esthetic properties and desirable physical properties to the composition. Generally, such optional ingredients are present in weight percentages ranging from about 0.1% to about 10% each, and from about 0.1% to about 20% in total, relative to the total weight of the composition.

For example, representative nonionic surfactants that can be included in the conditioning shampoo composition of the present invention include esters of polyols and sugars; the polyethoxylated and/or polypropoxylated alkylphenols; and the condensation products of ethylene oxide with long chain amides. All these nonionic surfactants, as well as numerous others not cited here, are well known in the art and are fully described in the literature.

The compositions of the present invention can be relatively viscous dispersions or emulsions that are stable to phase separation at a temperature of about 20° C. to about 25° C. for a period of time of at least 24 hours after preparation, and typically are stable to phase separation indefinitely at such temperatures. The emulsions should demonstrate sufficient stability to phase separation at temperatures normally found in commercial product storage and shipping to remain unaffected for period of one year or more.

The following examples illustrate various conditioning shampoos made in accordance with the present invention:

EXAMPLE 1

| | wt. % |
|---|---|
| 1. Water | 28.92 |
| 2. Methocel 40-101 (hydroxypropyl methylcellulose) (viscosity increasing agent) | 0.40 |
| 3. VERSENE® 100 (tetrasodium ethylene diamine tetracetic acid) (chelating agent) | 0.20 |
| 4. PEI-silicone copolymer (GLASSCLAD® IM) wt. av. mol. wt. = 900 (conditioning and stability) | 5.00 |
| 5. AROSURF TA 100 (distearyl dimonium chloride) (conditioning and stability) | 0.30 |
| 6. VARAMIDE® C-212 (cocamide MEA) (foam booster) | 1.25 |
| 7. CRODACID B (behenic acid) (100% active) (pH adjustment) | 1.25 |
| 8. DYNOL ALS Ammonium Lauryl Sulfate (anionic surfactant) | 40.00 |
| 9. SLES Sodium Lauryl Ether Sulfate (2 moles of ethoxylation) (anionic surfactant) | 20.00 |
| 10. VARION® CDG (foam booster) | 2.00 |
| 11. FRAGRANCE | 0.40 |
| 12. Kathon CG (preservative) | 0.08 |
| 13. GLYDANT (preservative) pH = 5.40 Viscosity (25° C.) = 6,000 cps. | 0.20 |

Comments: Good wet combing; excellent dry combing on damaged, e.g., permed, tinted, and dyed hair.

Mixing Procedure Example 1

Add the METHOCEL (#2) to water (#1) with high agitation for 20 minutes. Then add the VERSENE 100 (#3) and continue mixing while heating to 175°–180° F. Then add the PEI-silicone copolymer (#4) and the AROSURF (#5) and mix for 30 minutes while holding the temperature at 170° F. Then add the VERAMIDE G212 (#6), and the CRODACID (#7) and mix for 10–15 minutes or until lump-free. Then add the ammonium lauryl sulfate (#8) and the sodium lauryl ether sulfate (#9) and begin to cool the batch down to 110° F. Then add the VARION® CDG (#10), the fragrance (#11), the KATHON CG (#12), and the GLYDANT (#13).

EXAMPLE 2-5

| EXAMPLE | | 2 wt. % | 3 wt. % | 4 wt. % | 5 wt. % |
|---|---|---|---|---|---|
| 1. Water | | 57.10 | 56.60 | 55.60 | 47.60 |
| 2. Methocel 40-101 (hydroxypropyl methylcellulose) (viscosity increasing agent) | | 0.35 | 0.35 | 0.35 | 0.35 |
| 3. Ammonium Lauryl Sulfate (anionic surfactant) | | 35.00 | 35.00 | 35.00 | 35.00 |
| 4. MACKAMER™ BW-147 (PEI-silicone copolymer) | | 0.50 | 1.00 | 2.00 | 10.00 |
| 5. Cocacmide DEA FO (foam booster) | | 3.00 | 3.00 | 3.00 | 3.00 |
| 6. Glydant (preservative) | | 0.25 | 0.25 | 0.25 | 0.25 |
| 7. KATHON CG (preservative) | | 0.05 | 0.05 | 0.05 | 0.05 |
| 8. Perfume (fragrance) | | 0.50 | 0.50 | 0.50 | 0.50 |
| 9. Cold Pearl Mix | | 2.00 | 2.00 | 2.00 | 2.00 |
| sodium lauryl sulfate (30% active) | 1.32% | | | | |
| propylene glycol | 0.20% | | | | |
| Cocamide diethylamine | 0.04% | | | | |
| ethylene glycol monostearate | 0.40% | | | | |
| cetyl palmitate | 0.04% | | | | |
| Total | 2.00% | | | | |
| 10. Ammonium chloride (viscosity adjustment) | | 1.25 | 1.25 | 1.25 | 1.25 |
| | | 100.00 pH 8.50 | 100.00 pH 8.8 | 100.00 pH 8.9 | 100.00 pH 9.0 |
| Add liquid citric acid (50%) (pH adjustment) | | 0.20 | 0.20 | 0.25 | 0.25 |
| Final pH: | | 6.50 | 6.60 | 6.50 | 6.60 |
| Viscosity: | | 4,200 cps | 4,000 cps | 4,000 cps | 4,000 cps |

Procedure Examples 2-5

Disperse Methocel (#2) in water and mix for 25 minutes. Than add ALS (#3) and mix for 5 minutes. Add MACKAMER™ BW-147 (#4), continue mixing for ½ hour. Then add the remaining ingredients (#5-10) with mixing.

EXAMPLE 6

| | wt. % |
|---|---|
| 1. Water, Soft | 37.478 |
| 2. Liquid Citric Acid (50%) (pH adjustment) | 0.010 |
| 3. Methocel 40-100 (hydroxypropyl methylcellulose) (viscosity increasing agent) | 0.150 |
| 4. Water, soft | 2.000 |
| 5. Versene ® 100 | 0.200 |
| 6. Liquid Citric Acid (pH adjustment) | 0.160 |
| 7. DMDM Hydantoin (preservative) | 0.100 |
| 8. Kathon CG (preservative) | 0.050 |
| 9. Igepal ® CA 630 ($C_8H_{17}C_6H_4$ $(OCH_2CH_2)_9OH$) (solubilizer) | 0.750 |
| 10. Silwet ® L720 (silicone copolymer) (conditioner) | 0.001 |
| 11. Sodium Lauryl Sarcosinate (amphoteric surfactant) | 1.000 |
| 12. Propylene glycol (moisturizer) | 0.500 |
| 13. Wickenol 707/Macol CA 30P (emollients) | 0.001 |

-continued

| | wt. % |
|---|---|
| 14. Fragrance | 0.600 |
| 15. Dynol ALS (anionic surfactant) | 21.00 |
| 16. Surfactant Blend: (a) ALES (1 mole ethoxylation) (4.5%) (b) lauramide DEA (2.5%) (c) ammonium xylene sulfonate (0.6%) (d) water q.s. | 30.00 |
| 17. Tegobetaine L7 (amphoteric surfactant) | 3.00 |
| 18. MACKAMER™ BW-147 (PEI-silicone copolymer) | 2.00 |
| pH | 6.45 |
| viscosity | 6,000 cps |

Mixing Procedure Example 6

Add the Liquid Citric Acid (50%) (#2) to water (#1).
Add Methocel (#3) to the batch with high agitation for 20 minutes or mix until free of lumps.
Add #4, soft water.
Add #5, Versene® 100
Add #6, Liquid Citric Acid.
Add #7, DMDM hydantoin.
Add #8, KATHON CG.
Add #9, Igepal® CA 630.
Add #10, Silwet® L720.
Add #11, Sodium Lauryl Sarcosinate.
Add #12, Propylene Glycol.
Add #13, Wickenol 707.
Add #14, Fragrance.

Add #15, Dynol ALS.
Add #16, Surfactant Blend.
Add #17, Tegobetaine L7.
Add #18, MACKAMER™ BW-147.
Mix the batch for one (1) hour at room temperature 20°–25° C.

What is claimed is:

1. A conditioning shampoo for thoroughly cleansing and conditioning hair while maintaining foam comprising about 60% to about 90% water by total weight of the conditioning shampoo, an anionic surfactant in an amount of about 5% to about 65% by total weight of the conditioning shampoo; and a graft copolymer of polyethyleneimine on a polymethylsiloxane backbone as a conditioning agent in an amount of about 0.01% to about 20% by total weight of the conditioning shampoo, wherein the polyethyleneimine contains repeating units of $(CH_2CH_2NH)_n$, wherein n is about 15 to about 2500.

2. The conditioning shampoo of claim 1, wherein the anionic surfactant is a carboxylate surfactant.

3. The conditioning shampoo of claim 1 further including a long chain $(C_{12}-C_{22})$ amine oxide emulsion stabilizer in an amount of about 0.1% to about 5% based on the total weight of the conditioning shampoo.

4. The conditioning shampoo of claim 1 having a pH of about 4.5 to about 7.5.

5. The conditioning shampoo of claim 1, wherein the conditioning shampoo includes a viscosity increasing agent in an amount of about 0.1% to about 10% by weight, said conditioning shampoo having a viscosity of at least about 3,000 centipoises.

6. The conditioning shampoo of claim 1 further including a zwitterionic detergent in an amount of about 5% to about 25% by total weight of the conditioning shampoo.

7. The conditioning shampoo of claim 6, wherein the zwitterionic surfactant is a betaine surfactant.

8. The conditioning shampoo of claim 7, wherein the betaine surfactant is cocamidopropyl hydroxysultaine.

9. The conditioning shampoo of claim 1, wherein the conditioning shampoo includes about 5% to less than about 15% by total weight of the conditioning shampoo of an anionic surfactant selected from the group consisting of a long chain $(C_{12}-C_{22})$ alkyl sulfate; a long chain $(C_{12}-C_{22})$ alkyl ether sulfate; a long chain $(C_{12}-C_{22})$ alkyl sulfonate; and a long chain $(C_{12}-C_{22})$ alkyl ether sulfonate.

10. The conditioning shampoo of claim 1, wherein the polyethyleneimine grafted on the polymethylsiloxane backbone has a weight average molecular weight in the range of about 700 to about 70,000.

11. A method of cleansing and conditioning hair, simultaneously, while maintaining a substantial quantity of foam and excellent cleansing in a conditioning shampoo comprising contacting the hair with a conditioning shampoo comprising about 60% to about 90% water by weight of the conditioning shampoo; an anionic surfactant in an amount of about 5% to about 65% by total weight of the conditioning shampoo; and a graft copolymer of polyethyleneimine on a polymethylsiloxane backbone as a conditioning agent in an amount of about 0.01% to about 20% by total weight of the conditioning shampoo, wherein the polyethyleneimine contains repeating units of $(CH_2CH_2NH)_n$, wherein n is about 15 to about 2500.

12. The method of claim 11, wherein the anionic surfactant comprises an anionic carboxylate surfactant.

13. The method of claim 11, wherein the conditioning shampoo further includes a long chain $(C_{12}-C_{22})$ amine oxide emulsion stabilizer in an amount of about 0.1% to about 5% based on the total weight of the conditioning shampoo.

14. The method of claim 11, wherein the conditioning shampoo further includes a viscosity increasing agent in an amount of about 0.1% to about 10% by weight, said conditioning shampoo having a viscosity of at least about 3,000 centipoises.

15. The method of claim 11, wherein the conditioning shampoo further includes a zwitterionic detergent in an amount of about 5% to about 15% by total weight of the conditioning shampoo.

16. The method of claim 15, wherein the zwitterionic surfactant is a betaine surfactant in an amount of about 5% to about 25% by total weight of the conditioning shampoo.

17. The method of claim 16, wherein the betaine surfactant is cocamidopropyl hydroxysultaine.

18. The conditioning shampoo of claim 1, wherein n is about 15 to about 1500.

19. The conditioning shampoo of claim 1, wherein n is about 30 to about 1000.

20. The conditioning shampoo of claim 1, wherein the polyethyleneimine has a ratio of primary:secondary: tertiary nitrogen atoms of about 1:2:1.

* * * * *

UNITED STATES PATENT AND TRADEMARK OFFICE
CERTIFICATE OF CORRECTION

PATENT NO. : 5,556,616

DATED : September 17, 1996

INVENTOR(S) : Ben Janchitraponvej et al.

It is certified that error appears in the above-identified patent and that said Letters Patent is hereby corrected as shown below:

Title page, item [54] and
Column 1, 3rd line of the title, "COPOLYMERS" should be --COPOLYMER--.

Column 2, line 57, "Grote etal.;" should be --Grote et al.;--.

Column 5, line 44, "cocamdopropyl" should be --cocamidopropyl--.

Column 10, line 66, "lie" should be --like--.

Column 11, line 37, "ethyoxylated" should be --ethoxylated--.

Column 13, line 1, "EXAMPLE 2-5" should be --EXAMPLES 2-5--.

Column 13, line 37, "Than" should be --Then--.

Signed and Sealed this

Twenty-fifth Day of February, 1997

Attest:

BRUCE LEHMAN

*Attesting Officer*  *Commissioner of Patents and Trademarks*